US007987718B2

(12) United States Patent
Huber et al.

(10) Patent No.: US 7,987,718 B2
(45) Date of Patent: Aug. 2, 2011

(54) VIBROACOUSTIC SYSTEM FOR VIBRATION TESTING

(75) Inventors: Thomas M. Huber, St. Peter, MN (US); James F. Greenleaf, Rochester, MN (US); Mostafa Fatemi-Booshehri, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 732 days.

(21) Appl. No.: 11/721,845

(22) PCT Filed: Dec. 16, 2005

(86) PCT No.: PCT/US2005/045964
§ 371 (c)(1),
(2), (4) Date: May 7, 2008

(87) PCT Pub. No.: WO2006/069005
PCT Pub. Date: Jun. 29, 2006

(65) Prior Publication Data
US 2008/0302187 A1 Dec. 11, 2008

Related U.S. Application Data

(60) Provisional application No. 60/637,883, filed on Dec. 20, 2004.

(51) Int. Cl.
*G01H 9/00* (2006.01)
*G01H 13/00* (2006.01)

(52) U.S. Cl. .............. 73/579; 73/597; 73/602; 73/643; 73/655

(58) Field of Classification Search .............. 73/579, 73/597, 598, 602, 643, 655
See application file for complete search history.

(56) References Cited

U.S. PATENT DOCUMENTS

| 3,023,609 | A | * | 3/1962 | Schubring ................. 73/579 |
| 4,061,017 | A | * | 12/1977 | Sloane et al. ............. 73/579 |
| 5,505,090 | A | * | 4/1996 | Webster .................... 73/657 |
| 5,672,830 | A | | 9/1997 | Rogers et al. |
| 5,903,516 | A | * | 5/1999 | Greenleaf et al. .......... 367/92 |
| 5,974,881 | A | * | 11/1999 | Donskoy et al. ........... 73/579 |
| 5,991,239 | A | * | 11/1999 | Fatemi-Booshehri et al. ................. 367/164 |
| 6,068,597 | A | * | 5/2000 | Lin ........................ 600/443 |
| 6,711,954 | B2 | | 3/2004 | Drake, Jr. |
| 6,715,354 | B2 | | 4/2004 | Wooh |
| 2005/0075565 | A1 | * | 4/2005 | Satoh ........................ 600/437 |
| 2005/0165306 | A1 | * | 7/2005 | Zheng et al. ............ 600/437 |
| 2005/0167596 | A1 | * | 8/2005 | Rothenfusser et al. .... 250/341.6 |
| 2006/0000281 | A1 | * | 1/2006 | Harris ....................... 73/579 |
| 2006/0169029 | A1 | * | 8/2006 | Heyman .................... 73/52 |

OTHER PUBLICATIONS

International Search Report and Written Opinion corresponding to PCT/US2005/045964, under date of mailing of Jun. 21, 2006.

* cited by examiner

*Primary Examiner* — Hezron Williams
*Assistant Examiner* — Rose M Miller
(74) *Attorney, Agent, or Firm* — Quarles & Brady LLP

(57) ABSTRACT

Forces are applied to a device under test and its mechanical response is measured by a laser vibrometer (50). The forces are applied without making physical contact with the device by producing an acoustical force with an ultrasonic beam (54). One embodiment employs two confocal transducers (56, 58) that produce beams that flood the device. Drive signals modulate the ultrasonic beams to produce the desired forces, and the use on a plurality of ultrasonic beams enable selective excitation of different modes of vibration of the object (7).

19 Claims, 6 Drawing Sheets

VIBROACOUSTIC SYSTEM FOR VIBRATION TESTING

CROSS-REFERENCE TO RELATED APPLICATIONS

This application claims the benefit of U.S. Provisional patent application Ser. No. 60/637,883 filed on Dec. 20, 2004 and entitled "Vibroacoustic System For Vibration Testing".

BACKGROUND OF THE INVENTION

The field of the invention is vibration testing of articles of manufacture, and particularly, systems for vibrating very small items and observing the vibrational modes and resonances.

Non-contact vibration measurement using laser doppler vibrometry is a well-established technique. The laser doppler vibrometry method uses an interferometer to measure the doppler frequency shift induced by the vibration of the object. In order to measure the vibration of the object, the laser measurement beam strikes the object to be measured and interferes with a reference beam. The resulting frequency shift induced in the interference beam is the vibration of the target surface.

Micro-sensors and micro-actuators are the key components in a micro electrical mechanical system (MEMS). The performance of a micro-sensor or micro-actuator is determined in large part by the dynamic mechanical properties thereof. For instance, the bandwidth, resolution, and response time of some micro-sensors are determined by their mechanical resonance. The output characteristics of micro-actuators such as the force amplitude and the operating frequency thereof are also determined by their dynamic behaviors. Therefore, the testing method for evaluating the dynamic behaviors of the microstructures is very important. Several excitation and detection approaches have been developed to characterize the dynamic responses, vibration characteristics and the mode shapes of microstructures. Moreover, the material properties, e.g. residual stress, Young's modulus and fatigue properties, can also be determined.

The measured dynamic response of a microstructure will be affected by the technique used to vibrate the microstructure. FIG. 1 shows a conventional excitation device which drives the microstructure through built in electrostatic electrodes. The microstructure 10 formed on a silicon substrate 11 by a semiconductor manufacturing process is an insulator cantilever, for example, made of silicon oxide. In order to allow the cantilever 10 to be excited, a conductive film 12 such as a chromium film is applied over the insulator cantilever 10. Then, a variable-frequency sinusoidal voltage is applied between the silicon substrate 11 and the metallized line 12 leading to the cantilever 10 by way of a variable frequency oscillator 13. Accordingly, the cantilever 10 with the chromium film 12 can be electrostatically attracted toward the substrate with either voltage polarity so as to excite the mechanical motion of the cantilever 10. With this electrostatic approach, an additional conductive film which does not belong to the microstructure is deposited. Therefore, this test method is a destructive one. In addition, the presence of the additional film 12 may influence the dynamic behavior of the original cantilever 10.

FIG. 2 schematically shows another conventional excitation device which mechanically excites a microstructure. A test chip 20 with a microstructure (not shown) is attached onto a piezotransducer 21, and a voltage 22 is applied for driving the piezotransducer 21 so as to mechanically excite the physically attached test chip 20. The piezotransducer 21 is made of PZT. The natural frequencies of a PZT disc are strongly dependent on the ratio of diameter/thickness, and a PZT disc with finite dimensions has complex mode distributions in the frequency domain. As a result, when a PZT transducer acts as the excitation source applied to a microstructure, the spurious vibrational modes of the PZT transducer is strongly coupled with the dynamic responses of the microstructure. This dynamic coupling effect will interfere with the dynamic responses of the microstructure.

FIG. 3 shows a further conventional excitation device which uses a swept-sine signal to drive a microstructure. A specimen 31 with a microstructure (not shown) is attached to a PZT transducer 30. By providing a dynamic signal analyzer 32, a swept-sine signal is generated to drive the PZT transducer 30 and excite the specimen 31. A swept-sine signal generated by a dynamic signal analyzer typically has frequencies under 50 kHz so as to be suitable for a millimeter dimensional microstructure. As for a micron dimensional microstructure with higher natural frequencies, higher exciting frequencies will be required.

FIG. 4 shows a still further conventional excitation device which uses acoustic waves to excite a microstructure. A small loudspeaker 41 is mounted above a cantilever 40 to be excited. By providing AC power to the loudspeaker 41, the resulting acoustic waves 43 propagate via the air to the cantilever 40, causing the cantilever 40 to vibrate. The testing is limited to the frequency range of the loudspeaker 41 which can be much narrower than the desired vibrational frequencies.

SUMMARY OF THE INVENTION

The present invention is a method and apparatus for exciting vibrational modes in devices undergoing vibration testing, and more particularly, devices undergoing non-contact laser vibrometry. Two ultrasonic transducers are employed and their respective beams are directed on to the device being tested where they mix to produce a controlled radiation force on the device. The frequency and phase of the radiation force is precisely controlled by the frequency and phase of the two ultrasonic beams to precisely excite vibrations in the device under test.

A general object of the invention is to provide non-contact excitation of the device under test. The two ultrasonic transducers do not physically contact the device under test, but instead, the ultrasonic beams which they produce mix at a location on or in the device to produce the excitation force. As a result, the vibrational modes of the device are not influenced by external driving apparatus and the vibrations sensed by the laser vibrometer are due solely to the mechanical properties of the device under test.

Another object of the invention is to apply a precise excitation force to the device under test. The two ultrasonic beams can be focused and steered to a very precise location on the device under test. The frequency difference between the two beams determines the frequency of the applied radiation force, and these two frequencies can be carefully controlled.

Another aspect of the invention is the application of two forces to a device under test by producing two modulated ultrasonic beams. The two beams can be either focused or unfocused and they can be frequency or amplitude modulated by a drive signal having a desired frequency to produce a force at a desired frequency. By shifting the phase of the drive signals, the force can be oriented in different directions to evoke transverse or torsional motion in the device.

GENERAL DESCRIPTION OF THE INVENTION

The present invention takes advantage of a radiation force that is produced by two intersecting sonic beams or by a radiation force produced by an amplitude modulated sonic beam. Producing forces in this manner is particularly useful in that ultrasonic frequencies can be used that are not heard by human operators. Consider an ultrasonic source directing its beam on a target. The radiation force, F, for the plane wave case is commonly written as $$F = KP/c, \quad (1)$$

where P, c and K are the total time averaged acoustic power, sound speed and a constant, respectively. The value of K for a perfectly absorbing target is 1, and for a perfectly reflecting target it is 2. For a focused beam impinging on a partially reflecting target of arbitrary size, the linear relation of (1) still holds, however, the value of K is different and can be determined as a function of target power reflection coefficient and its size as directed by J. Wu, "Calculation Of Acoustic Radiation Force Generated By Focused Beams Using The Ray Acoustic Approach," *J. Acoust. Soc. Am.* 97(5), pt. 1, May 1995.

Figure 1:
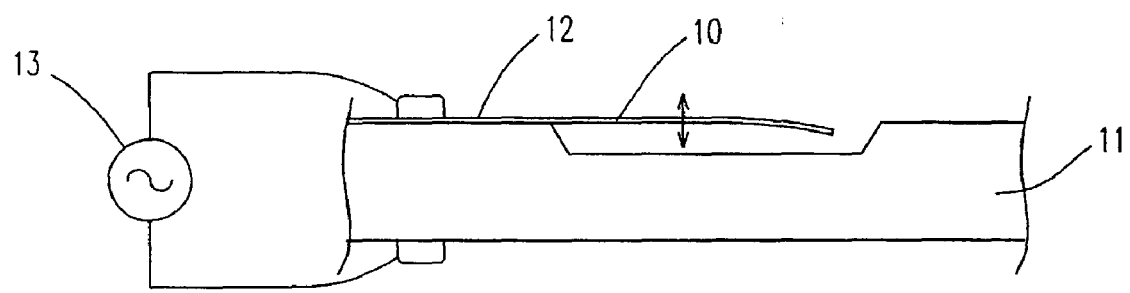
FIG. 1 is a schematic diagram showing a first conventional excitation device which drives the microstructure through built in electrostatic electrodes.
Figure 2:
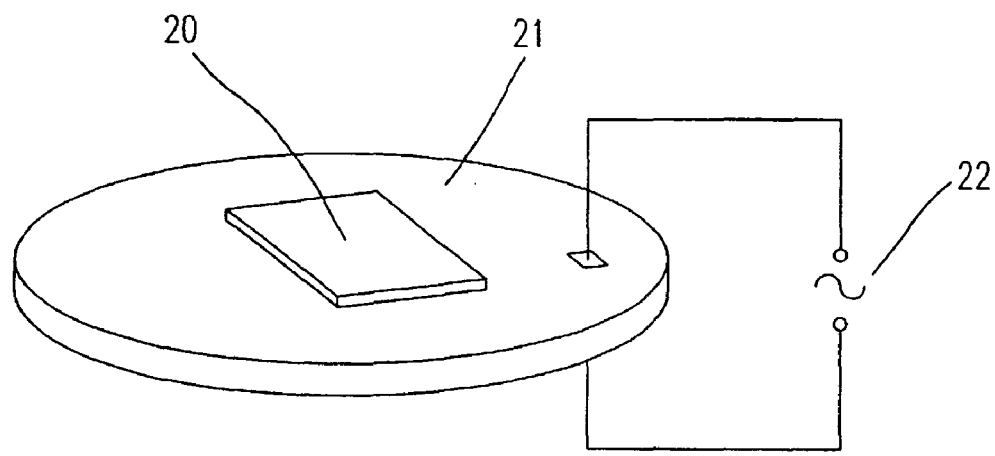
FIG. 2 is schematic diagram showing a second conventional excitation device which mechanically excites a microstructure.
Figure 3:
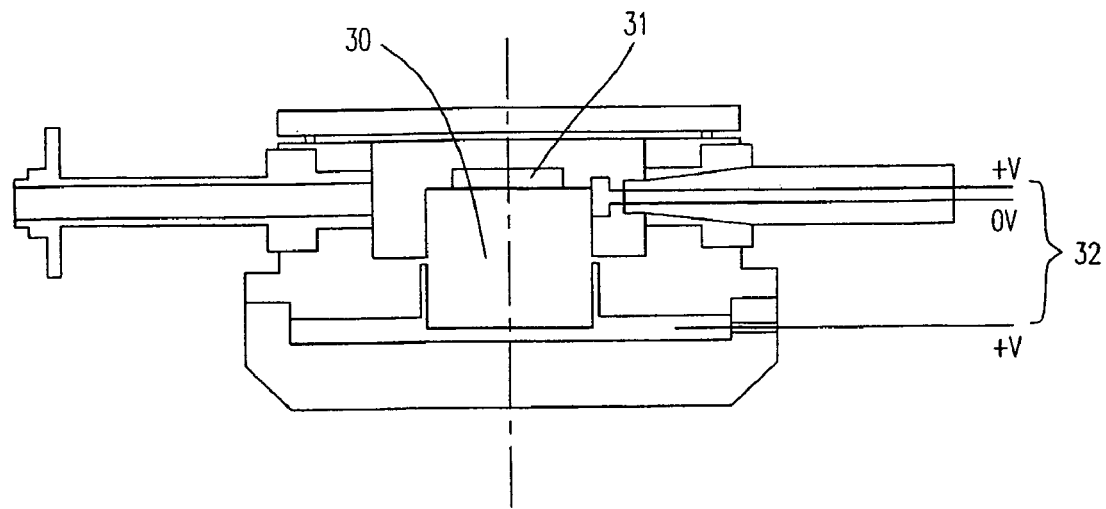
FIG. 3 is schematic diagram showing a third conventional excitation device which uses a swept-sine signal to drive a microstructure.
Figure 4:
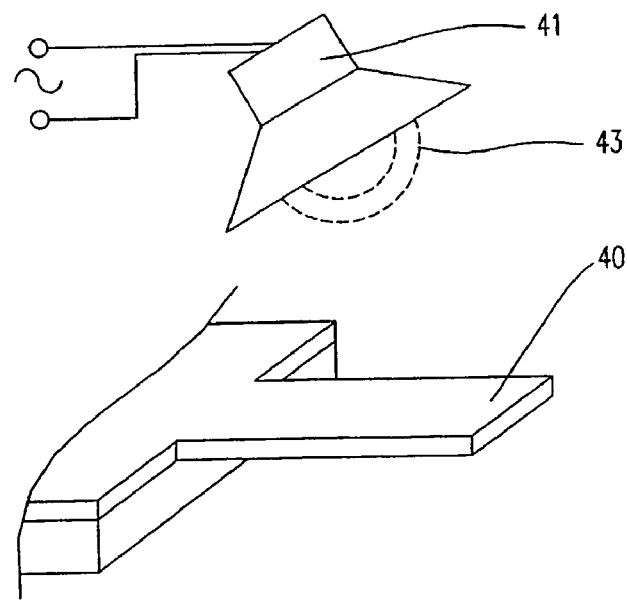
FIG. 4 is schematic diagram showing a fourth conventional excitation device which uses acoustic waves to excite a microstructure.
Figure 5:
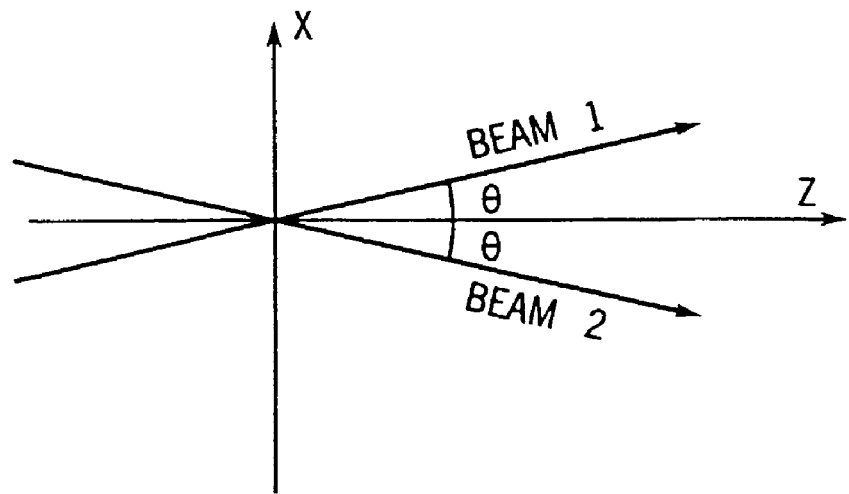
FIG. 5 is a graphic illustration of two intersecting sonic beams.

Consider two plane wave beams propagating in two directions on the (x,z) plane, crossing each other at the origin as shown in FIG. 5. To simplify the problem, we assume that these beams have equal amplitude and phase, and propagate at θ and −θ angles with respect to the z-axis. Also, we assume that both profiles on the z=0 plane are identical and equal to g(x,y). The resultant field on the z=0 plane may be written as $$s(t) = g(x,y)[\cos(\omega_1 t - k_1 \sin\theta) + \cos(\omega_2 t + k_2 \sin\theta)], \quad (2)$$

where $k_1 = \omega_1/c$ and $k_2 = \omega_2/c$. Assuming $\Delta\omega = \omega_1 - \omega_2 \ll \omega_1, \omega_2$, then it can be shown that the acoustic power has slow variations at the "beat" frequency $\Delta\omega$ about its long time average. Denoting this beam frequency component by $P_1(t,x,y)$, we can write $$P_1(t,x,y) = g^2(x,y)\cos[\Delta\omega t - (k_1 + k_2)x\sin\theta]. \quad (3)$$

Now consider a planar target on the z=0 plane. Referring to Eq. (1), the normal component of radiation force exerted on this target by $P_1(t,x,y)$ may be found by the following integration:

$$F_1(t) = \frac{K}{c} \int\int P_1(t, x, y) dx dy. \quad (4)$$

The result of this integration is a sinusoidal function of time at the beat frequency $\Delta\omega$. This beat force vibrates the target, resulting in a new pressure field at this frequency.

Figure 6:
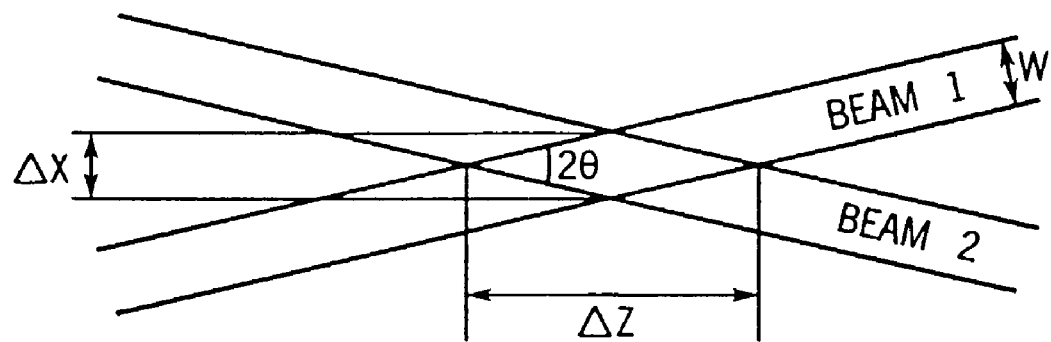
FIG. 6 is a graphic illustration of a region formed by the intersecting beams of FIG. 5.

Referring particularly to FIG. 6, a two transducer assembly produces two focused beams of width w that intersect about their focal points at an angle 2θ. The above plane wave approximation applies because the interaction region is limited to the focal area. The resolution of the system may be defined as the interaction area where the two beams overlap. In this example, Δx and Δz represent the lateral and axial resolutions, respectively. Assuming identical beam widths, w, the resolution can be written Δx=ω/cos θ and Δz=ω/sin θ. These values are full-width at quarter-maximum (FWQM) estimates because w is defined on a full-width at half-maximum (FWHM) basis.

Within the interaction area the beat force indicated by Eq. (4) will be applied to the object. The manner in which the object responds to this force will, of course, depend on its mechanical characteristics and this response may be measured with a laser vibrometer as will be described below The present invention may also be implemented by a system in which the high frequency field is generated by a single, ultrasonic source (single element or array of elements) driven by an amplitude modulated signal. The carrier frequency is ω and the modulating signal, h(t), is defined as:

$$h(t) = \sqrt{u(t)}, \quad (5)$$

where $$u(t) = 1 + f(t). \quad (6)$$

The signal f(t) is a low frequency signal. We assume |f(t)|<1, also we assume that the bandwidth of f(t) is much less than the carrier frequency ω.

We assume the beam is propagating along the z-axis. The field on the z=0 plane can be written as $$s(t) = g(x,y)h(t)\cos(\omega t), \quad (7)$$

where g(x,y) is the beam profile on the z=0 plane. It can be shown that the acoustic power density has slow variations about its long time average. Denoting this component by $P_1(t,x,y)$, we can write $$P_1(t, x, y) = \frac{1}{2}g^2(x, y)h^2(t). \quad (8)$$

Assuming a target is present at z=0 plane, then the radiation force exerted on this target by $P_1(t,x,y)$ may be found by the following integration:

$$F_t(t) = \frac{K}{c} \int\int P_1(t, x, y) dx dy. \quad (9)$$

The result of this integration is a function proportional to $h^2(t) = 1 + f(t)$. The time-varying component of this force vibrates the target proportional to the signal f(t). The target displacement due to this force, r(t), may be written as $$r(t) = \frac{1}{2}K'f(t) \tag{10}$$

where K' is a constant whose value depends on size, power reflection coefficient, and other mechanical parameters of the target, such as mass and damping factors, that determine its response to a given force.

Within the target area the force indicated by Equation (9) will be applied to the object. The manner in which the object responds to this force will, of course, depend on its mechanical characteristics and this response may be measured with a laser vibrometer as will be described below.

DETAILED DESCRIPTION OF THE PREFERRED EMBODIMENT

Figure 7:
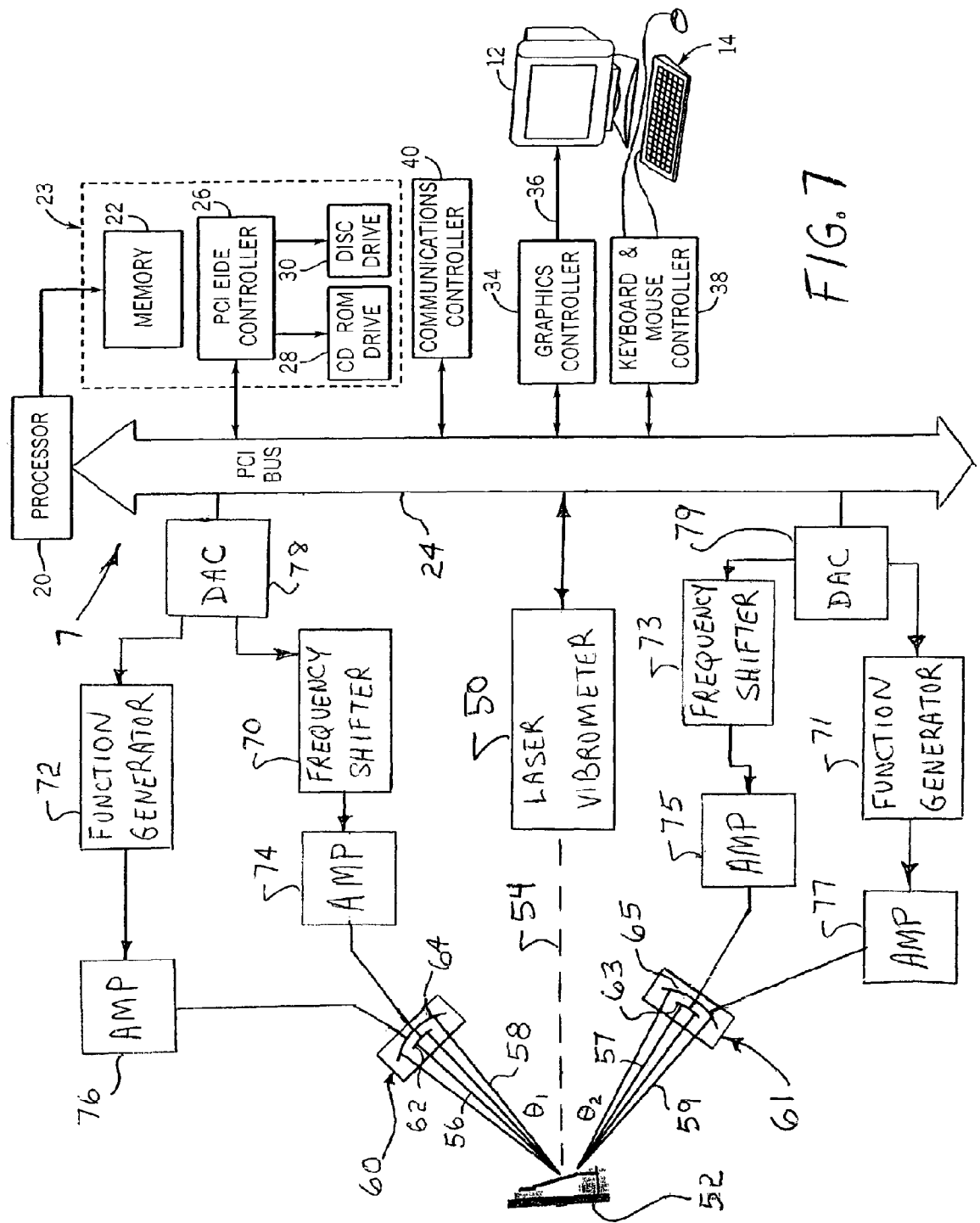
FIG. 7 is a block diagram of a first embodiment of a system that employs the present invention.

Referring particularly to FIG. 7, a first preferred embodiment of the vibration testing system is controlled by a computer workstation indicated generally at 7. The computer workstation 7 includes a processor 20 which executes program instructions stored in a memory 22 that forms part of a storage system 23. The processor 20 is a commercially available device designed to operate with one of the Microsoft Corporation Windows operating systems. It includes internal memory and I/O control to facilitate system integration and integral memory management circuitry for handling all external memory 22. The processor 20 also includes a PCI bus driver which provides a direct interface with a PCI bus 24.

The PCI bus 24 is an industry standard bus that transfers 32-bits of data between the processor 20 and a number of peripheral controller cards. These include a PCI EIDE controller 26 which provides a high-speed transfer of data to form a CD ROM drive 28 and a disc drive 30. A graphics controller 34 couples the PCI bus 24 to a CRT monitor 12 through a standard VGA connection 26, and a keyboard and mouse controller 38 receives data that is manually input through a keyboard and mouse 14.

The PCI bus 24 also connects to a communications controller 40. The controller 40 connects to an intranet that links the workstation 7 to other institution systems.

A laser vibrometer 50 is coupled to the workstation 7 and is controlled thereby to examine the vibrations in a device 52. The vibrometer 50 is a commercially available product such as the model PSV-400 commercially available from Polytec Incorporated. It emits a laser beam indicated by dashed line 54 which strikes a region on the device 52 and it receives the light reflected back. As is well known in the vibrometer art, the reflected light is examined and from the phase information therein the motion of the device 52 can be determined. Other detection methods may be employed to detect vibration including electronic sensing of the motion of the object, acoustic re-emission, or optical holography.

To excite vibratory motion in the device 52 two ultrasonic beams 56 and 58 are produced by a confocal ultrasonic transducer 60 and aimed at one point on the device 52 and two ultrasonic beams 57 and 59 are produced by a second confocal ultrasonic transducer 61 and aimed at a second point on the device 52. As described in U.S. Pat. No. 5,991,239, issued on Nov. 23, 1999 and entitled "Confocal Acoustic Force Generator", these transducers 60 and 61 include two separate ultrasonic, phased array transducers 62/64 and 63/65 that emit focused ultrasonic beams 56/58 and 57/59 that converge at their respective focal points. As described in that patent which is incorporated herein by reference, this focal point may be electrically steered over the surface of the device 52 to excite a small, well defined area.

The transducers 62/64 in the confocal transducer 60 are driven by respective amplifiers 74 and 76. Amplifier 76 is driven by a function generator 72 which produces an ultrasonic carrier signal $\omega_c$ at a frequency determined by a command signal received from the workstation 7 through a digital to analog converter (DAC) module 78. The amplifier 75 is driven by a frequency shifter 70 which generates an ultrasonic carrier signal $\omega_c+\omega$ in response to a command received from the workstation 7. The two transducers 62/64 in the confocal transducer 60 are thus driven at two ultrasonic frequencies that differ in frequency by the amount $\omega$. As will be explained below, the two beams 56 and 58 mix at their common focal point and the difference frequency $\omega$ produces a force $\vec{F}_1$ that oscillates at this frequency $\omega$.

The confocal transducer 61 is driven in the same manner as the transducer 60. Amplifiers 75 and 77 drive respective transducers 63 and 65 and a function generator 71 produces an ultrasonic carrier signal $\omega_c$ in response to commands from workstation 7 through DAC 79. A frequency shifter 73 produces the signal $\omega_c+\omega$ applied to amplifier 75.

The confocal transducers 60 and 61 may thus produce separately controlled forces $\vec{F}_1$ and $\vec{F}_2$ at two respective focal points on the device under test 52. A net force is thus produced $\vec{F}_{NET}=\vec{F}_1+\vec{F}_2$ and the laser vibrometer 50 is positioned to measure the resulting movement of the device 52 and input the results to the workstation 7.

This net force can be broken into its components parallel and perpendicular to the normal of the device's surface:

$$\vec{F}_{NET}=(\vec{F}_{1,\|}+\vec{F}_{2,\|})\hat{n}_\|+(\vec{F}_{1,\perp}+\vec{F}_{2,\perp})\hat{n}_\perp \tag{11}$$

where $$F_{1,\|}=F_1 d_\| \cos\theta_1; F_{1,\perp}=+F_1 d \sin\theta_1$$

$$F_{2,\|}=F_2 d_\| \cos\theta_2; F_{2,\perp}=+F_2 d \sin\theta_2 \tag{12}$$

The factors $d_\|$ and $d_\perp$ are drag coefficients in the normal and transverse directions; they may or may not be unity, and they might not be identical.

Therefore, the net force can be written as:

$$\vec{F}_{NET}=(F_1 \cos\theta_1+F_2 \cos\theta_2)d_\|\hat{n}_\|+(F_1 \sin\theta_1-F_2 \sin\theta_2)d_\perp\hat{n}_\perp \tag{13}$$

Now, if the driving force is sinusoidal with a frequency $\omega$, which is the audio-range difference frequency, the forces can be written as:

$$F_1=F \cos(\omega t), \text{ and, } F_2=aF \cos(\omega t+\phi)$$

where "a" is a scaling factor between the two transducers (a=1 corresponds to equal amplitude), and $\phi$ is the phase difference between the driving forces $F_1$ and $F_2$. This phase difference is controlled by the commands to the frequency shifters 70 and 73. This means that the net force can be written as $$\vec{F}_{NET} = \begin{matrix} F[\cos(\omega t)\cos\theta_1 + a\cos(\omega t+\phi)\cos\theta_2]d_\|\hat{n}_\| + \\ F[\cos(\omega t)\sin\theta_1 + a\cos(\omega t+\phi)\sin\theta_2]d_\perp\hat{n}_\perp \end{matrix} \tag{14}$$

Consider the special case:
a=1 (Equal amplitude beams)
$\phi$=0 (No Phase Difference)

$\theta_1=\theta_2$ (Equal Angles of Incidence)
Then the net force on the object is completely along the direction of the normal $$\vec{F}_{NET}=2Fd_\| \cos(\omega t)\cos\theta_1 \hat{n}_\|. \qquad (15)$$

Similarly, if two equal amplitude beams are 180° out of phase,
a=1 (Equal Amplitude Beams)
$\phi=\pi$ (180° out of phase)
$\theta_1=\theta_2$ (Equal angles of incidence)
then the resultant force is completely in the transverse direction $$\vec{F}_{NET}=2Fd_\perp \cos(\omega t)\sin\theta_1 \hat{n}_\perp \qquad (16)$$

Therefore, depending on the phase of the driving force, the motion can either be normal to the surface, in the transverse direction, or any arbitrary direction in a 2-d plane. The ability to selectively excite both in-plane and out-of-plane vibrations is a unique capability of this embodiment of the invention.

If a third transducer is added to the system of FIG. 7, it is possible to excite vibrations in the device 52 in three directions, x, y and z. The ability to induce vibrations in different orthogonal directions is useful in testing devices, such as MEMs accelerometers or strain gauges, with sensing elements in two or three dimensions. It may also be used to study the mechanical properties, such as Young's Modulus, of anisotropic materials, or for detection of defects such as delaminations in materials.

The present invention may also be used to suppress selected motions or modes of vibration of the device under test. For example, to suppress a particular torsion mode of vibration in a cantilevered device, one may apply forces thereto on two sides of the cantilever to enable vibration in a bending mode but not in the torsion mode.

Figure 8:
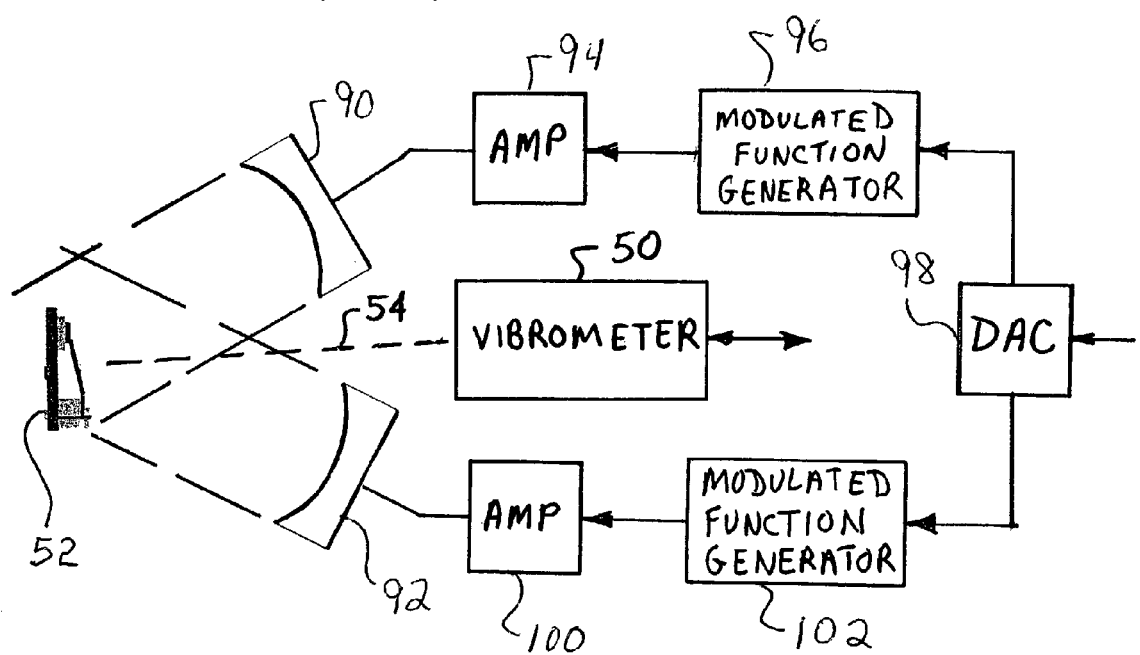
FIG. 8 is a partial block diagram of a second embodiment of a system that employs the present invention.

Referring particularly to FIG. 8 a second embodiment of the invention employs two ultrasonic transducers 90 and 92 which each produce an unfocused beam with a central carrier frequency $\omega_c$. The transducers 90 and 92 are aimed such that their beams strike the surface of the device 52 being examined to produce a force. The resulting motion of the device 52 is examined by a vibrometer 50 as in the first embodiment described above.

The transducers 90 and 92 each produce an amplitude modulated carrier that produces a force on the device 52 as set forth above in Equation (9). The transducer 90 is driven by an amplifier 94 which in turn receives an amplitude modulated carrier signal from a modulated function generator 96. The function generator 96 produces a carrier signal at the frequency $\omega_c$ (e.g., 500 kHz) and the amplitude of this carrier signal is modulated by an audio signal $h_1(t)$ received from a digital-to-analog converter 98. Similarly, the transducer 92 is driven by an amplifier 100 which receives an amplitude modulated carrier from a modulated function generator 102. The modulator 102 also receives an audio signal $h_2(t)$ from DAC 98. The DAC 98 and vibrometers 50 are connected to the above-described workstation 7 and both the driving signals $h_1(t)$ and $h_2(t)$ are under software control. Thus, forces $f_1(t)$ and $f_2(t)$ related to the two driving signals $h_1(t)$ and $h_2(t)$ (i.e., $h^2(t)=1+f(t)$) can be applied to the device 52 and its mechanical response measured by the vibrometer 50. In the preferred embodiment the carrier $\omega_c$ is suppressed, however, this is not a necessity.

The carrier frequencies $\omega_c$ of the two transducers 90 and 92 are set the same in the preferred embodiment such that no significant beat frequency between carrier frequencies is produced in the region in which their beams overlap. Also, the frequency of the modulating signal $h_1(t)$ and $h_2(t)$ may be the same, but their phases may differ in order to change the phase of the oscillatory forces each produces on the surface of the device 52. In particular, if the two transducers are driven in phase, they will selectively excite transverse modes of a cantilever-like object while suppressing torsional modes. Similarly, when the two transducers are driven such that they produce a radiation force that is out-of-phase, it will selectively excite torsional modes while suppressing transverse modes. This capability may be useful for testing of objects with nearly degenerate transverse and torsional modes of vibration. While the same carrier frequency $\omega_c$ is preferred for both transducers 90 and 92, it is also possible to drive them at substantially different frequencies such that the resulting beat frequency will not interfere with the examination. For example, carrier frequencies of 400 kHz and 600 kHz will produce a 200 kHz beat frequency which is well above the audio range in which mechanical resonances reside.

Figure 9A:
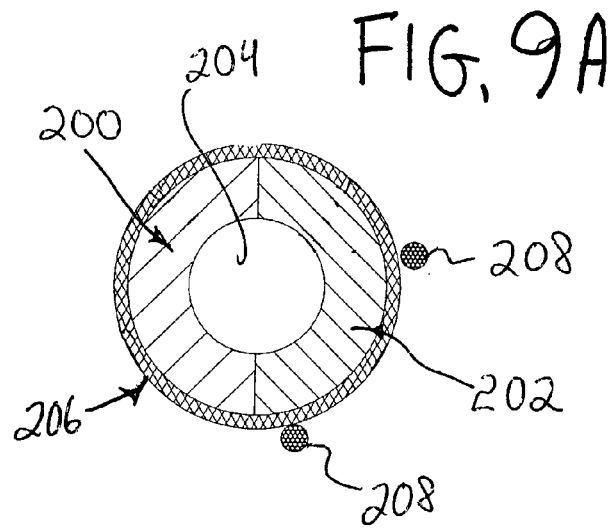
FIGS. 9A-C are pictorial representations of ultrasonic transducers that may be used with the present invention.
Figure 9B:
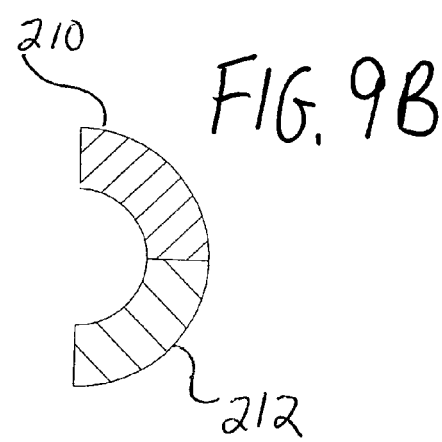
Figure 9C:
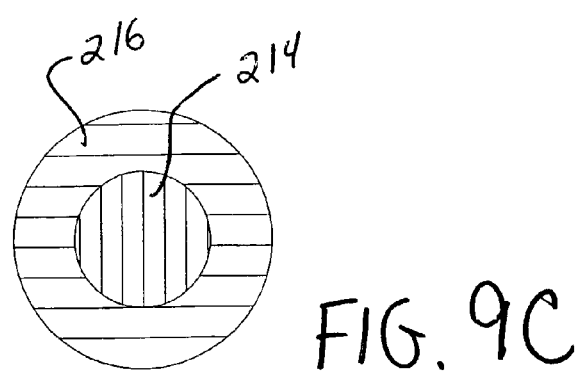

While available ultrasonic transducers may be used in either of the above embodiments, preferably the transducers are adapted for this application. Referring to FIGS. 9A-C the transducer assembly in FIG. 9A includes two ultrasonic transducers 200 and 202 which together form an annular ring around a central opening 204. A lens of a laser vibrometer may be disposed in the central opening 204. An illumination device in the form of a ring of light emitting diodes 206 may also be formed around the annular transducers 202 and 200. To facilitate aiming of the transducer two or more laser diodes 208 or similar devices are mounted adjacent the transducers 200/202. Their two visible beams converge at the ultrasonic focus point. The transducers 200/202 may form a single annular ring, or they may form two or more segmented arcs, each of which is driven with a different ultrasound signal. Each transducer segment may produce a beam which is converging, diverging, or neutral focus. If the beams are converging, they may be electronically steered to focus at the same or different points on the device under test.

The alternative transducer assembly in FIG. 9B is comprised of two ultrasonic transducers 210 and 212 which together form an arc rather than a complete ring. Two of such structures may be used to form a complete ring and provide four separate ultrasonic transducers and beams that can be steered to points on the device under test. The ultrasonic transducers 214 and 216 in FIG. 9C are confocal transducers such as those described in U.S. Pat. No. 5,991,239 except the beams produced by transducers 214 and 216 can be steered to focus at two different locations to allow more selective excitation of the device under test.

Any of the above described embodiments of the invention can be used for modal testing of objects. In addition to being completely non-contact, the techniques that are employed enable selective excitation of the device under test that is not possible using a mechanical shaker. The selective excitation enables unprecedented control over the type of mode to be studied. If it is desired to focus on torsional modes, this can be accomplished under software control by changing the phase of a driving signal. Similarly, a range of frequencies can easily be tested by changing the frequencies of the driving signals under software control. It is also possible to excite the tested device at multiple frequencies applied simultaneously. For example, in the embodiment of FIG. 8 one of the function generators can be modulated at one frequency and the other function generator can be modulated at a different frequency. In addition, the modulating waveform that produces the excitation force may be sinusoidal, pulsed, or another waveform shape. Therefore, for a particular device 52 a test program may be developed for the workstation 7 which tests the mechanical response of the device 52 at a series of known resonant frequencies and for both transverse and torsional resonances. The resulting measurements made by the laser vibrometer are compared to threshold values that are used to pass or fail the device 52 or classify the device 52. Since the force(s) applied to the tested device is determined by the driving signal(s), these same driving signals or a derivative thereof can be used as a reference signal for the vibrometer 50. This reference signal may be input to the vibrometer reference port, or to a phase lock-in amplifier, coherent detector, programmable filter, or similar devices, to extract the desired motion signal at the intended vibration frequency thus suppressing noise and other unwanted signals produced by the vibrometer.

It should be apparent to those skilled in the art that a number of variations can be made from the preferred embodiments described above without departing from the spirit of the invention. For example, more than two ultrasound beams may be directed at the object under test. By varying the frequency and/or phase of these beams complex mechanical resonances may be explored. Also, ultrasound travels well through different mediums and the object under test may be submerged in a liquid or embedded in another object which serves as a media.

The invention claimed is:

1. A method for measuring the mechanical properties of a device, the steps comprising:
   a) producing a first sonic beam and directing the first sonic beam on the device;
   b) modulating the first sonic beam with a first drive signal to produce a corresponding force that acts on the device;
   c) producing a second sonic beam and directing the second sonic beam on the device;
   d) modulating the second sonic beam with a second drive signal to produce a corresponding force that acts on the device;
   e) measuring the mechanical response of the device to the forces acting on it without physically contacting the device in such a manner that would alter its mechanical response; and
   wherein the phase of one of said drive signals is changed to excite a different mode of mechanical response of the device.

2. The method as recited in claim 1 in which step e) is performed by using a laser vibrometer.

3. The method as recited in claim 1 in which the frequency of each drive signal is changed to measure the mechanical response of the device to forces applied to it at different frequencies.

4. The method as recited in claim 1 in which step a) includes:
   a)i) focusing the first sonic beam; and
   a)ii) directing the focus at a first location on the device; and in which step c) includes:
   c)i) focusing the second sonic beam; and
   c)ii) directing the focus at a second location on the device.

5. The method as recited in claim 4 in which step a) includes producing two sonic beams that are focused on the first location, and step b) includes modulating the frequency of one of said two sonic beams with the first drive signal.

6. The method as recited in claim 5 in which step c) includes producing two sonic beams that are focused on the second location, and step d) includes modulating the frequency of one of said two sonic beams with the second drive signal.

7. The method as recited in claim 1 in which step b) is performed by amplitude modulating the first sonic beam with the first drive signal.

8. The method as recited in claim 7 in which step d) is performed by amplitude modulating the second sonic beam with the second drive signal.

9. The method as recited in claim 1 which includes:
   f) producing a third sonic beam and directing the third sonic beam on the device; and
   g) modulating the third sonic beam with a third drive signal to produce a corresponding force that acts on the device.

10. The method as recited in claim 1 in which the sonic beams pass through a gaseous medium to reach the device.

11. The method as recited in claim 1 in which the sonic beams pass through a liquid medium to reach the device.

12. A method for measuring the mechanical properties of a device, the steps comprising:
   a) producing a first ultrasonic beam and directing the first ultrasonic beam on the device;
   b) modulating the first ultrasonic beam with a first drive signal to produce a corresponding force that acts on the device;
   c) producing a second ultrasonic beam and directing the second ultrasonic beam on the device;
   d) modulating the second ultrasonic beam with a second drive signal to produce a corresponding force that acts on the device;
   e) measuring the mechanical response of the device to the forces acting on it; and
   wherein the phase of one of said drive signals is changed to excite a different mode of mechanical response of the device.

13. The method as recited in claim 1 in which step e) is performed by using a laser vibrometer.

14. The method as recited in claim 12 in which the frequency of each drive signal is changed to measure the mechanical response of the device to forces applied to it at different frequencies.

15. The method as recited in claim 12 in which step a) includes:
   a)i) focusing the first ultrasonic beam; and
   a)ii) directing the focus at a first location on the device; and in which step c) includes:
   c)i) focusing the second ultrasonic beam; and
   c)ii) directing the focus at a second location on the device.

16. The method as recited in claim 15 in which step a) includes producing two ultrasonic beams that are focused on the first location, and step b) includes modulating the frequency of one of said two ultrasonic beams with the first drive signal.

17. The method as recited in claim 12 in which step b) is performed by amplitude modulating the first ultrasonic beam with the first drive signal.

18. The method as recited in claim 17 in which step d) is performed by amplitude modulating the second ultrasonic beam with the second drive signal.

19. The method as recited in claim 18 in which the phase of one of said drive signals is changed to excite a different mode of mechanical response of the device.

* * * * *